(12) United States Patent
Benes et al.

(10) Patent No.: US 6,512,136 B1
(45) Date of Patent: Jan. 28, 2003

(54) SUBSTITUTED 2-PHENYL-1-(3,4-DIHYDROXY-5-NITROPHENYL)-1-ETHANONES, THEIR USE IN THE TREATMENT OF SOME CENTRAL AND PERIPHERAL NERVOUS SYSTEM DISORDERS AND PHARMACEUTICAL COMPOSITIONS CONTAINING THEM

(75) Inventors: Jan Benes, Maia (PT); Patricio Manuel Viera Araujo Soares Da Silva, Oporto (PT); David Alexander Learmonth, Maia (PT)

(73) Assignee: Portela & C.A., S.A., S. Mamde do Coronado (PT)

( * ) Notice: Subject to any disclaimer, the term of this patent is extended or adjusted under 35 U.S.C. 154(b) by 0 days.

(21) Appl. No.: 09/464,813

(22) Filed: Dec. 17, 1999

(30) Foreign Application Priority Data

Dec. 18, 1998 (GB) .............................................. 9827996

(51) Int. Cl.⁷ ...................... C07C 69/76; C07C 291/00; C07C 239/00
(52) U.S. Cl. ...................... 560/108; 560/136; 564/299; 564/300
(58) Field of Search .......................... 568/337; 560/108, 560/136; 564/299, 300

(56) References Cited

FOREIGN PATENT DOCUMENTS

| EP | 0237929 | 11/1987 |
|---|---|---|
| FR | 2607493 | 11/1987 |

OTHER PUBLICATIONS

Backstrom et al., "Synthesis of Some Novel Potent and Selective Catechol O–Methyltransferase Inhibitors," J. Med. Chem. 1989, pp. 841–846, vol. 32, No. 4.

*Primary Examiner*—Paul J. Killos
(74) *Attorney, Agent, or Firm*—Rankin, Hill, Porter & Clark LLP (57) ABSTRACT

New compounds of formula I are described

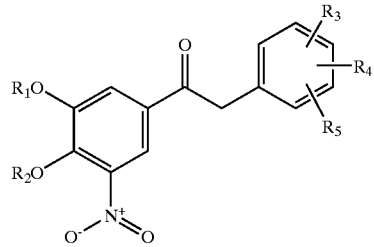

The compounds have potentially valuable pharmaceutical properties in the treatment of some central and peripheral nervous system disorders, where a reduction in the O-methylation of catecholamines may be of therapeutical benefit, such as Parkinson's disease and parkinsonian disorders, gastrointestinal disturbances, edema formation states and hypertension.

12 Claims, 3 Drawing Sheets

SUBSTITUTED 2-PHENYL-1-(3,4-DIHYDROXY-5-NITROPHENYL)-1-ETHANONES, THEIR USE IN THE TREATMENT OF SOME CENTRAL AND PERIPHERAL NERVOUS SYSTEM DISORDERS AND PHARMACEUTICAL COMPOSITIONS CONTAINING THEM

The most effective symptomatic treatment of Parkinson's disease involves the administration of L-β-3,4-dihydroxyphenylalanine (L-DOPA), the immediate precursor of dopamine. Orally administered L-DOPA is predominantly metabolised in the periphery by aromatic L-amino acid decarboxylase (AADC) to dopamine, which can cause serious adverse effects such as emesis, orthostatic hypotension and cardiac arrhythmia. Therefore, L-DOPA is usually administered in combination with a peripheral AADC inhibitor (benserazide or carbidopa). When administered together with such inhibitors, very little dopamine is formed in the periphery, but only a small amount of an oral dose of L-DOPA reaches the brain because a considerable amount of the drug undergoes methylation to, 3-O-methyl-L-DOPA (Männistö, P. A., et al., Progress Drug Research, 39: 291–350, 1992). The duration of the L-DOPA-induced clinical improvement is brief as a result of the short half-life of L-DOPA, which contrasts with the long half-life of 3-O-methyl-L-DOPA. Within a few years after starting L-DOPA therapy with the customary 2 to 4 doses per day, L-DOPA-induced clinical improvement wanes at the end of each dose cycle, producing the "end-of-dose" or "wearing-off" pattern of motor fluctuations. A close relationship has been described between accumulation of 3-O-methyl-L-DOPA and development of the "wearing-s off" phenomenon (Tohgi, H., et al., Neurosci. Letters, 132:19–22, 1992). It has been anticipated that this might result from inhibition of L-DOPA transport at the level of the blood-brain barrier by its O-methylated metabolite (Reches, A., et al., Neurology, 32:887–888, 1982) or simply because there is less L-DOPA available to reach the brain (Nutt, J. G., Fellman, J. H., Clin. Neuropharmacol., 7:35–49, 1984).

In recent years, the development of new inhibitors of the enzyme catechol-O-methyl transferase (COMT) has been accelerated by the hypothesis that inhibition of this enzyme may provide significant clinical improvements in patients afflicted by Parkinson's disease undergoing treatment with L-DOPA plus a peripheral AADC inhibitor. The rationale for the use of COMT inhibitors is based on their capacity to inhibit the O-methylation of L-DOPA to 3-O-methyl-L-Dopa. COMT inhibition slows elimination of L-DOPA from the plasma by increasing plasma half-life (increases area under the curve [AUC] without altering the time L-DOPA plasma to peak or the maximum concentration). Thus pharmacokinetic alterations may be an advantage over increasing the dose of L-DOPA, which also increases AUC, but additionally raises peak concentrations. In turn, raising peak concentrations relates to adverse effects such as dyskinesia, which occurs immediately when COMT inhibitors are given but can be anticipated by either reducing the dose of L-DOPA or increasing the time intervals between doses. The effects of COMT inhibition also differ from those of controlled-release L-DOPA formulation which slow down absorption and reduce bioavailability. The pharmacokinetic changes induced by COMT inhibition reduce the daily L-DOPA dose by enabling a reduction of each dose or an increase in dose intervals. With repeated doses of L-DOPA every 2–6 h in the presence of COMT inhibition, the mean plasma L-DOPA concentration is raised and the through concentrations are increased proportionally more than the peak concentrations despite a reduction in L-DOPA dose. As would be predicted by the slowed elimination of L-DOPA, the duration of antiparkinsonian action with single doses of L-DOPA is prolonged by COMT inhibition (Nutt, J. G., Lancet, 351:1221–1222, 1998).

The most potent and selective COMT inhibitors found so far are very active and do not interact with other enzymes, receptors, ionic channels or transporters up to very high doses. Some of them were demonstrated to have beneficial effects both in experimental models of parkinsonism and in Parkinson's disease patients. Other therapeutic applications of these COMT inhibitors have also been put forward, namely in the treatment of depression or anxiety, as gastroprotective drugs and as natriuretic and antihypertensive agents.

The most potent COMT inhibitors thus far reported, 3,4-dihydroxy4'-methyl-5-nitrobenzophenone (tolcapone, Australian Pat. AU-B-69764/87), and (E)-2-cyano-N,N-diethyl-3-(3,4-dihydroxy-5-nitrophenyl)acrylamide (entacapone, German Pat. DE 3740383 A 1) have inhibition constants in the low nM range. Tolcapone differs from entacapone in being a more potent inhibitor of COMT in the periphery and furthermore at penetrating into the brain to inhibit brain COMT as well. It has not been established which of these two inhibitors is more useful in the treatment of Parkinson's disease. Compounds penetrating the blood-brain barrier may be assumed to be more effective as theoretically they might have additional benefits of decreasing dopamine methylation to 3-methoxytyramine and homovanillic acid. Conversely, central inhibition may be unimportant if the more significant action is to protect L-DOPA from breakdown in the periphery. This distinction may have practical importance, as the use of COMT inhibitors which are excluded from the brain may avoid potential undesired CNS side effects of these agents.

In this respect, it is interesting to underline the lack of antiparkinsonian action of tolcapone when given alone (Hauser, R. A., et al., Mov Disord, 1998, 13, 643–647), and the relatively frequent observations of increased central dopaminergic stimulation, primarily dyskinesia and confusion, in patients taking L-DOPA plus tolcapone (Nuft, J. G., Lancet, 351:1221–1222, 1998). This suggests that the central effects of COMT inhibition are very small when given alone, but when given with L-DOPA the risk of inhibition of brain COMT may be associated with the appearance of symptoms related to increased dopaminergic stimulation which may require cessation of therapy.

Another potential problem with COMT inhibitors concerns their relatively short half-life (tolcapone, 2 h [Dingemanse, J., et al., Clin. Pharmacol. Ther., 57:508–517, 1995]; entacapone, 0.3 h [Keranen, T., et al., Eur. J. Clin. Pharmacol., 46:151–157, 1994]). To circumvent this problem both tolcapone and entacapone are recommended to be administered as frequently as 3 times a day; because the half-life of entacapone is considerably shorter than that of tolcapone, the recommended dose for entacapone is twice that for tolcapone.

As previously mentioned, the 3,4-dihydroxy-5-nitrophenyl group was identified as an active pharmacophore and it was simultaneously discovered that the presence of a carbonyl group (e.g. in tolcapone ) or enone group (e.g. in entacapone) conjugated to the pharmacophore of the molecule generally enhances inhibition of the COMT catalysed transfer of the methyl group from the S-adenosyl-L-methionine coenzyme to a substrate containing a catechol functional group. Among many tested compounds bearing a 3,4-dihydroxy-5-nitrobenzoyl group, the corresponding benzophenones were recognized as the most potent COMT inhibitors with $ED_{50}<1$ mg/kg (rat, p.o.) (Borgulya J. et al., Helvetica Chimica Acta 72, 952–968, 1989).

Formation of homologues of known biologically active compounds as potentially improved drugs is a well known principle and is used mainly for optimization of activity of structurally nonspecific drugs or for achieving changes in predominant biological action in structurally specific drugs (Korolkovas A. Essentials of Medicinal Chemistry, p. 76, 1988 by J. Wiley & Sons, Inc.). On the other hand, homologation is not generally used nor expected to influence predictably the half-life of a compound.

We have surprisingly proven that the next higher homologue of 3,4-dihydroxy-5-nitrobenzophenone i.e. the compound with one more methylene group between the substituted benzoyl group and phenyl group is endowed with selective COMT inhibition of long duration and that this effect is unique in a series of the higher homologues.

The invention relates to substituted 2-phenyl-1-(3,4-dihydroxy-5-nitrophenyl)-1-ethanones of formula I where $R_1$ and $R_2$ are hydrogens or groups hydrolysable under physiological conditions, the same or different, and signify optionally substituted lower alkanoyl or aroyl, optionally substituted lower alkyl or arylsulphonyl or optionally substituted lower alkylcarbamoyl, or taken together signify a lower alkylidene or cycloalkylidene group; $R_3$, $R_4$ and $R_5$ are the same or different and signify hydrogen, optionally substituted saturated or partially unsaturated lower hydrocarbon residue, hydroxyl, optionally substituted lower alkoxy or aryloxy group, optionally substituted aryl, optionally substituted alkanoyl or aroyl group, lower alkanoylamino group, lower dialkanoylamino group, carboxyl, optionally substituted lower alkyloxycarbonyl or aryloxycarbonyl group, optionally substituted carbamoyl, halogen, nitro, amino, lower alkylamino or lower dialkylamino or cyano group, or taken together signify aliphatic or heteroaliphatic rings or aromatic or heteroaromatic rings, and pharmaceutical acceptable salts thereof; to the use of the compounds for prevention or treatment of certain pathological states in humans and to the preparation of pharmaceutical compositions containing them.

The term "lower" denotes residues with a maximum of 8, preferentially a maximum of 4 carbon atoms. The term "alkyl" taken alone or in combination with terms such as "alkanoyl, alkoxycarbonyl, alkylidene, cycloalkylidene, alkoxycarbonyloxy, alkylamino" denotes straight-chain or branched saturated hydrocarbon residues. The term halogen denotes fluorine, chlorine, bromine, and iodine. The term "aryl" denotes a carbocyclic aromatic group, preferably mono- or bicyclic groups.

For the preparation of pharmaceutical compositions of compounds of formula I, inert pharmaceutically acceptable carriers are admixed with the active compounds. The pharmaceutically acceptable carriers may be either solid or liquid. Solid form preparations include powders, tablets, dispersible granules and capsules. A solid carrier can be one or more substances which may also act as diluents, flavouring agents, solubilizers, lubricants, suspending agents, binders or tablet disintegrating agents; it may also be an encapsulating material.

Preferably, the pharmaceutical preparation is in unit dosage form, e.g. packaged preparation, the package containing discrete quantities of preparation such as packeted tablets, capsules and powders in vials or ampules.

The dosages may be varied depending on the requirement of the patient, the severity of the disease and the particular compound being employed. For convenience, the total daily dosage may be divided and administered in portions throughout the day. Determination of the proper dosage for a particular situation is within the skill of those in the medical art.

Reference is now made to the accompanying drawings in which.

Figure 1:
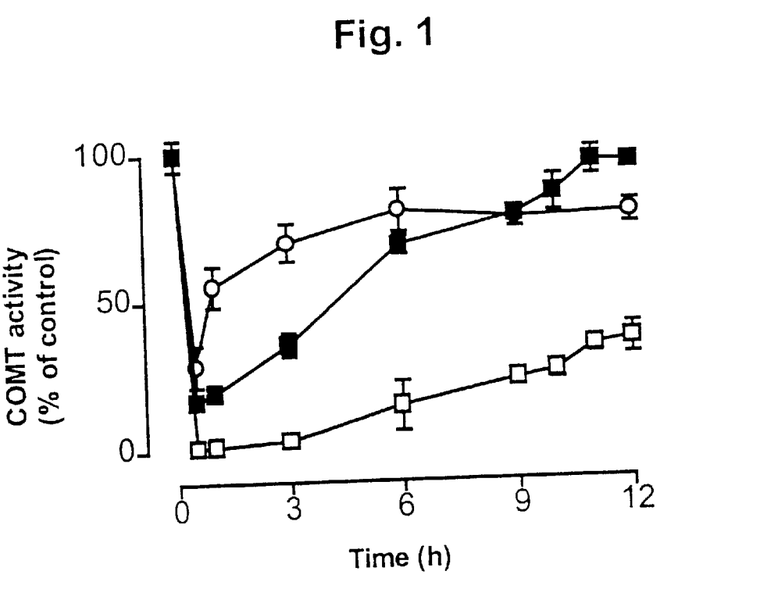
FIG. 1 is a graph showing brain COMT activity at different times after oral administration of compound B (closed squares), entacapone (open circles) or tolcapone (open squares).
Figure 2:
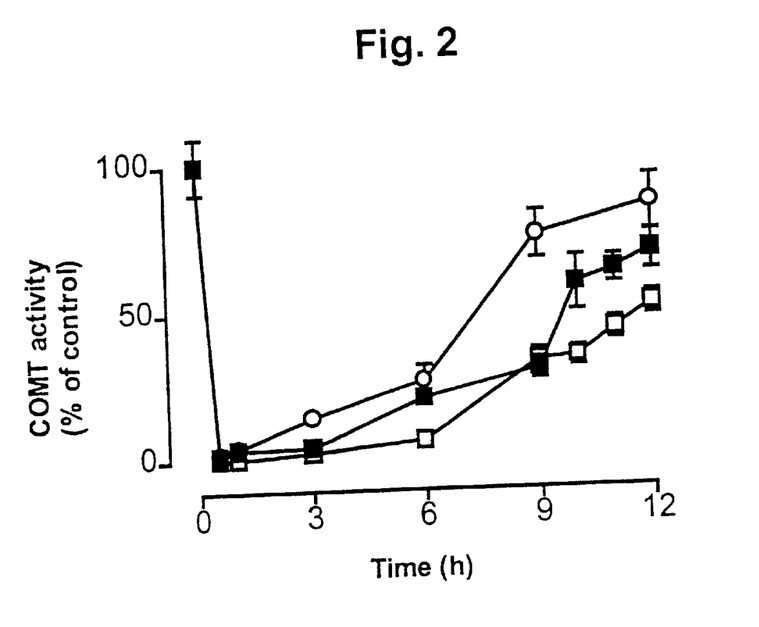
FIG. 2. is a graph showing liver COMT activity at different times after oral administration of compound B (closed squares), entacapone (open circles) or tolcapone (open squares).

In FIGS. 1 and 2 each point represents the mean of four to eight experiments per group and vertical lines the respective SEM.

Figure 3:
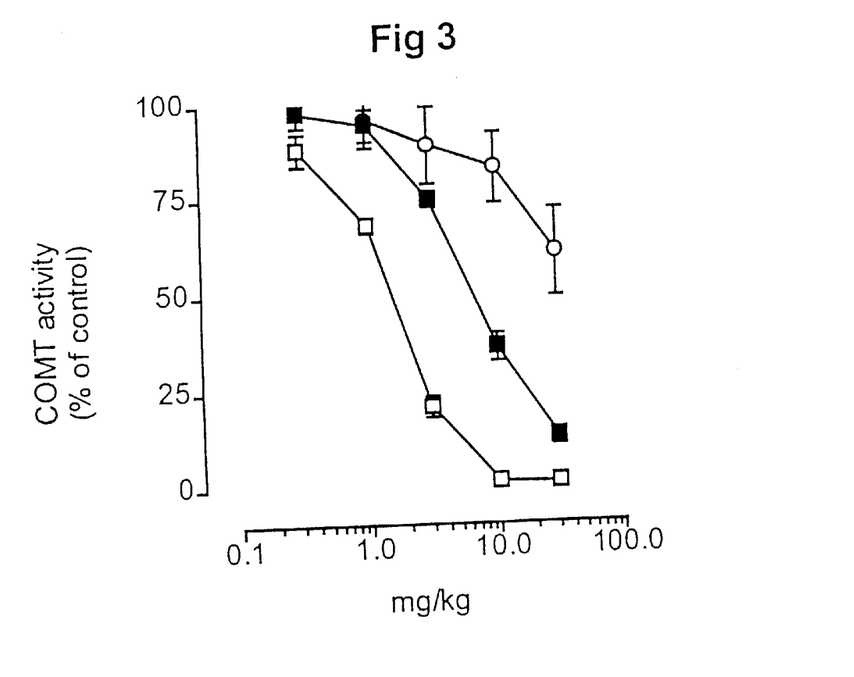
FIG. 3 is a graph showing concentration dependent inhibition of brain COMT activity at one hour after oral administration of compound B (closed squares), entacapone (open circles) or tolcapone (open squares).
Figure 4:
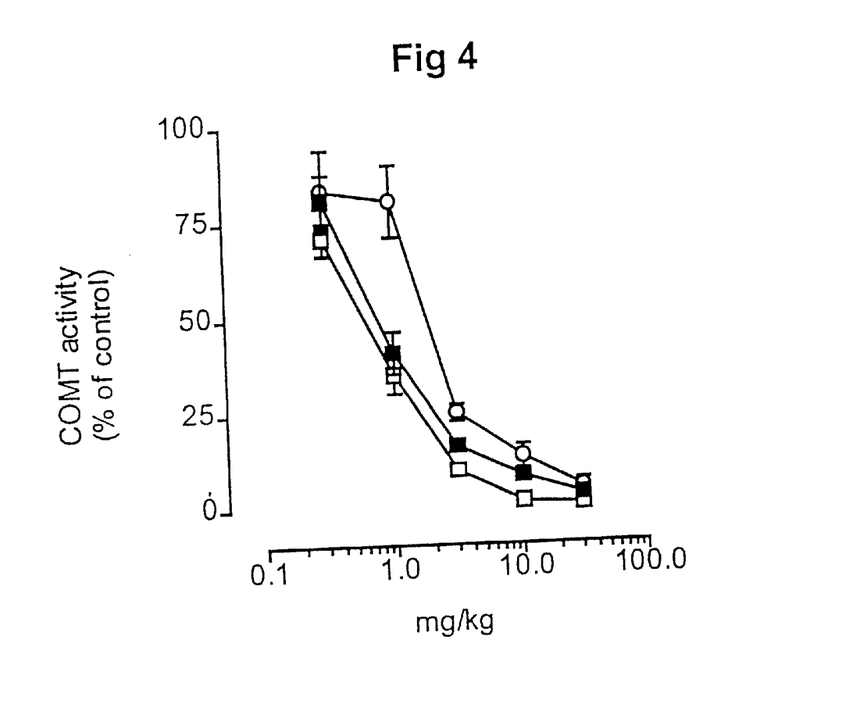
FIG. 4 is a graph showing concentration dependent inhibition of liver COMT activity at one hour after oral administration of compound B (closed squares), entacapone (open circles) or tolcapone (open squares).

In FIGS. 3 and 4 each point represents the mean of eight experiments per group and vertical lines the respective SEM.

Figure 5:
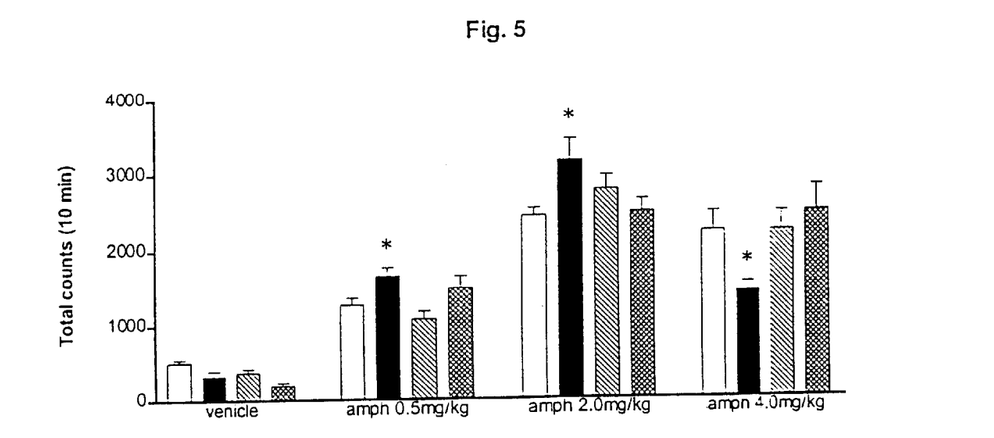
FIG. 5 is a graph showing concentration-dependent amphetamine-induced horizontal activity after oral administration of vehicle (open columns), tolcapone (closed columns), entacapone (hatched columns) and compound B (cross hatched columns).
Figure 6:
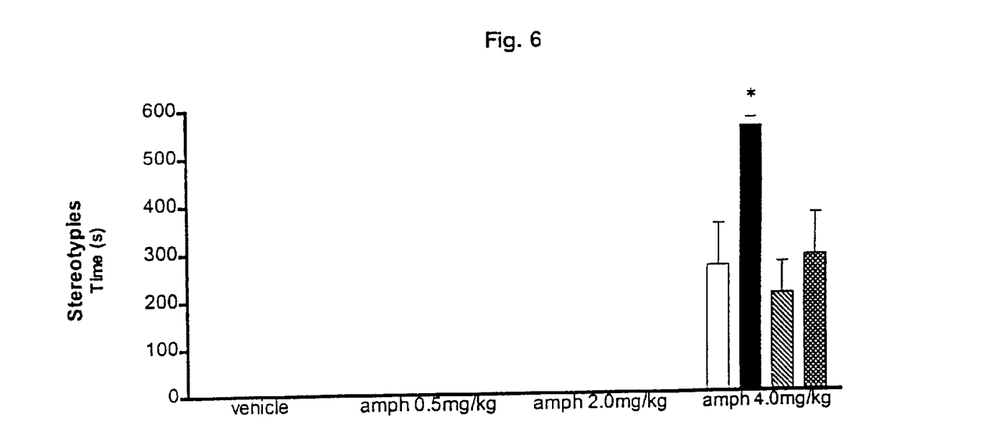
FIG. 6 is a graph showing concentration-dependent amphetamine is induced stereotypes after oral administration of vehicle (open columns), tolcapone (closed columns), entacapone (hatched columns) and compound B (cross hatched columns).

In FIGS. 5 and 6 each column represents the mean of eight experiments per group and vertical lines the respective SEM.

MATERIALS AND METHODS

Assay of COMT Activity

Livers and brains from 60 day old male Wistar rats weighing 240–260 g (Harlan-Interfauna Ibérica, Barcelona, Spain), kept two per cage under controlled environmental conditions (12 h light/dark cycle and room temperature 24° C.) were used in all experiments. After decapitation, the organs were immediately removed and homogenised in 5 mM phosphate buffer of pH 7.8. COMT activity was evaluated by the ability to methylate adrenaline to metanephrine. Aliquots of 0.5 ml of liver and whole brain homogenates were preincubated for 20 min with 0.4 ml of phosphate buffer (5 mM); thereafter, the reaction mixture was incubated for 15 min with increasing concentrations of epinephrine (0.1 to 2000 µM; 0.1 ml) in the presence of a saturating concentration of S-adenosyl-L-methionine, the methyl donor (brain, 100 µM; liver, 500 µM); the incubation medium contained also pargyline (100 µM), $MgCl_2$ (100 µM) and EGTA (1 mM). The preincubation and incubation were carried out at 37° C. under conditions of light protection with continuous shaking and without oxygenation.

In experiments conducted with the aim of studying the inhibitory effect of COMT inhibitors on enzyme activity, the reaction mixture was preincubated for 20 min with increasing concentrations of test compounds (0.5 to 1,000 nM); the incubation was performed in the presence of a concentration of adrenaline five times the corresponding $K_m$ value as determined in saturation experiments.

In experiments designed to evaluate the oral bioavailability, half-life and brain access, test compounds were given by gastric tube to overnight fasted rats. Thereafter, at defined intervals, animals were killed by decapitation and livers and brains removed and used to determine COMT activity as described above.

At the end of the incubation period (brain, 15 min; liver, 5 min) the tubes were transferred to ice and the reaction was stopped by the addition of 200 µl of 2 M perchloric acid. The samples were then .centrifuged (200×g, 4 min, 4° C.), and 500 µl aliquots of the supernatant, filtered on 0.22 µm pore size Spin-X filter tubes (Costar) were used for the assay of metanephrine.

The assay of metanephrine was carried out by means of high pressure liquid chromatography with electrochemical detection. The lower limits for detection of metanephrine ranged from 350 to 500 mmol (0.5 to 1.0 mmol/mg protein/h).

$K_m$ and $V_{max}$ values for COMT activity were calculated from non-linear regression analysis using the GraphPad Prism statistics software package (Motulsky, H. G., et al., GraphPad Prisms, GraphPad Prism Software Inc., San Diego, 1994). For the calculation of the $IC_{50}$ values, the parameters of the equation for one site inhibition were fitted to the experimental data. Geometric means are given with 95% confidence limits and arithmetic means are given with S.E.M. Statistical analysis was performed by one-way analysis of variance (ANOVA) using Newman-Keuls multiple comparison test to compare values.

The protein content in the homogenates was determined by the method of Bradford (Bradford, M. M., Anal. Biochem., 72: 248–254, 1976) with human serum albumin as standard. The protein content was similar in all samples (approximately 5 mg/500 µl homogenate).

Behavioural Testing

The experimental design used in the present study was aimed at determining the potentiation of amphetamine-induced hyperactivity of brain dopaminergic systems by COMT inhibitors. For this purpose 128 rats were divided into 16 groups, and were given the vehicle or one of the three COMT inhibitors tested 6 hours prior to behavioural evaluation. In all groups of rats, behavioural testing started 15 min after the s.c. injection of vehicle or increasing doses of amphetamine (0.5, 2.0 or 4.0 mg/kg).

On the test day, 7 h before the experiment began, animals were transferred to a dimly illuminated and sound attenuating room separate from the animal colony room where the test cages were kept; temperature and humidity were the same as in the colony room. Spontaneous locomotor activity was measured using a San Diego Instruments rodent activity monitor (model Flex Field, San Diego Instruments, San Diego, Calif.) with 48 infrared motion sensors. The lower frame was 50.5×50.5 cm, with 32 photocells (separated by 2.5 cm) located lengthwise 5 cm above the floor. The upper frame was 50.5×5 50.5 cm, with 16 photocells (separated by 2.5 cm) located lengthwise 15 cm above the floor. The test field was an acrylic chamber with internal dimensions 40×40×37 cm. Ten-minute activity recording began immediately after placing the test subject at the centre of the chamber. Activity was measured automatically with a personal computer using Flex Field software (San Diego Instruments) which provides user-defined intervals of total interruptions. Three parameters of normal spontaneous locomotion were recorded: horizontal activity, vertical activity and centre time. Stereotypical behaviour (intense sniffing, repetitive head and limb movements and licking and biting, as defined by Feldman, R. S., Meyer, J. S., Quenzer, L. F., Principles of Neuropharmacology, 1997, Sinauer Associates, Inc. Publishers, Sunderland, Mass.) were quantified by an independent observer after being recorded on tape by means of video tracking system (VP200, HVS Image, Ltd) placed 70 cm above the test field. Animals were habituated to the test field environment for one hour prior to behavioural testing.

RESULTS

In vitro COMT Inhibition Studies

Incubation of liver and whole brain homogenates in the presence of increasing concentrations of adrenaline resulted in a concentration-dependent formation of metanaphrine, yielding $K_m$ (in µM) and $V_{max}$ (in nmol mg protein$^{-1}$ h$^{-1}$) values of 0.7 (0.5, 0.9; 95% confidence intervals) and 1.35±0.02 for brain and 238.5 (128.5; 348.5) and 61.6±3.8 for liver, respectively. From these kinetic parameters, a saturating concentration of adrenaline was chosen to use in inhibition studies (liver, adrenaline=1000 µM; brain, adrenaline=100 µM). Compounds of formulae A–E,

| n | Compound |
|---|----------|
| 0 | A |
| 1 | B |
| 2 | C |
| 3 | D |
| 4 | E | plus entacapone and tolcapone (the reference compounds) produced a concentration-dependent decrease in O-methylation of adrenaline with $IC_{50}$ values in the low nM range for the brain and in the µM range for the liver (see Table 1).

TABLE 1

IC$_{50}$ values (in nM) for inhibition of rat brain and liver COMT.

| Compound | Brain | Liver |
|---|---|---|
| A | 7.1 (3.4, 14.8) | 935 (511, 1710) |
| B | 3.7 (1.7, 8.1) | 696 (356, 1360) |
| C | 3.1 (1.1, 8.9) | 829 (498, 1379) |
| D | 2.9 (1.4, 6.1) | 1852 (758, 4522) |
| E | 6.7 (3.5, 12.9) | 1285 (673, 2454) |
| Entacapone | 12.8 (4.0, 41.3) | 2320 (741, 7263) |
| Tolcapone | 2.2 (0.8, 6.4) | 927 (551, 1561) |

Compounds of formulae A–E were found to be potent inhibitors of both brain and liver COMT, the maximal inhibitory effect being achieved within 30 min after their oral administration (table 2). Compound A presented a similar inhibitory profile in brain and liver COMT, whereas compound E was much more potent upon liver COMT than brain COMT. Similarly, compound B was also much more potent as a peripheral COMT inhibitor than in brain. Compounds with longer carbon chains were less potent at inhibiting brain COMT in comparison with their effects upon liver COMT. This difference may have to do with difficulties in access to brain. Compounds with short carbon chains (A, B and C) were not equally potent at inhibiting peripheral and central COMT, but this difference was not so striking as observed with compounds with long carbon chains. When looking at the duration of inhibitory effect upon liver COMT it became evident that compound B (2 carbon chain) was a particularly long acting compound. Notably, inhibition of liver COMT by this compound at 9 h after oral administration almost achieved 70% inhibition, whereas compounds with shorter and longer carbon chains were not endowed of such a long acting effect. Tolcapone at 6 h and 9 h after administration produced marked inhibition in brain and liver COMT. As shown in FIGS. 1 and 2, nine hours after administration, compound B and tolcapone were equally potent at inhibiting liver COMT, whereas entacapone was almost devoid of COMT inhibitory properties. On the other hand, compound B and entacapone were much less potent than tolcapone at inhibiting brain COMT.

TABLE 2

Percent inhibition of COMT activity by compounds A–E, entacapone (Enta) and tolcapone (Tolc) in homogenates of rate brain and liver, determined at 0.5, 1, 3, 6 and 9 h after their administration by gastric tube. Results are means ± S.E.M. of 4 experiments per group.

| | % inhibition Time course | | | | |
|---|---|---|---|---|---|
| | 0.5 h | 1 h | 3 h | 6 h | 9 h |
| Brain | | | | | |
| A | 96.3 ± 0.4 | 96.8 ± 0.3 | 97.0 ± 0.3 | 85.8 ± 7.5 | 34.9 ± 6.0 |
| B | 83.6 ± 1.3 | 80.9 ± 2.7 | 65.0 ± 3.9 | 31.5 ± 3.2 | 21.9 ± 2.7 |
| C | 89.9 ± 0.7 | 86.2 ± 0.5 | 59.8 ± 5.8 | 33.4 ± 7.0 | 0.4 ± 5.3 |
| D | 85.1 ± 1.7 | 69.3 ± 5.1 | 33.5 ± 4.4 | 26.7 ± 4.0 | 12.2 ± 5.8 |
| E | 87.4 ± 1.3 | 74.2 ± 4.2 | 25.0 ± 3.1 | −5.6 ± 7.5 | −6.7 ± 5.0 |
| Enta | 71.7 ± 7.0 | 44.8 ± 7.0 | 30.1 ± 6.4 | 19.9 ± 7.1 | 22.8 ± 3.4 |
| Tolc | 98.9 ± 0.1 | 98.7 ± 0.2 | 97.0 ± 0.5 | 85.8 ± 8.2 | 77.5 ± 1.8 |
| Liver | | | | | |
| A | 99.0 ± 0.2 | 98.7 ± 0.2 | 96.9 ± 2.5 | 80.5 ± 7.3 | 31.7 ± 5.5 |
| B | 98.6 ± 0.4 | 96.7 ± 1.7 | 96.2 ± 0.8 | 75.9 ± 4.2 | 69.8 ± 3.6 |
| C | 98.4 ± 0.3 | 97.8 ± 0.2 | 95.0 ± 0.7 | 70.8 ± 12.8 | 39.9 ± 11.1 |
| D | 97.5 ± 0.1 | 95.3 ± 0.8 | 67.5 ± 7.8 | 52.0 ± 9.5 | 39.0 ± 13.2 |
| E | 99.2 ± 0.1 | 98.9 ± 0.3 | 88.1 ± 3.9 | 36.0 ± 6.3 | −4.0 ± 8.0 |
| Enta | 98.2 ± 0.3 | 96.2 ± 1.1 | 85.9 ± 2.2 | 73.6 ± 5.4 | 24.7 ± 7.9 |
| Tolc | 100.0 ± 0.0 | 99.9 ± 0.1 | 98.0 ± 0.7 | 94.1 ± 0.3 | 67.0 ± 4.0 |

Compounds F–J (see below) were also tested at 6 h and 9 h after administration and found to produce an inhibitory profile similar to that described for compound B. (Table 3).

| Compound | Ar |
|---|---|
| F |  |
| G |  |
| H |  |
| I |  |
| J |  |

The potency of compound B, tolcapone and entacapone at inhibiting brain and liver COMT was evaluated in experiments in which rats were given increasing doses of the compounds under test (0.3 to 30 mg/kg). In these experiments rats were killed 1 h after the administration of the compounds (at $t_{max}$) and COMT activity determined as described above. The results obtained are shown in FIGS. 3 and 4 and indicate that compound B and tolcapone were equally potent at inhibiting liver COMT with $ED_{50}$'s of 0.7±1.1 and 0.7±0.1 mg/kg, respectively; entacapone was slightly less potent with a $ED_{50}$ value of 1.9±0.2 mg/kg,. However, compound B was less potent than tolcapone at inhibiting brain COMT with $ED_{50}$'s of 5.3±1.1 and 1.6±0.1 mg/kg, respectively. At the highest dose tested (30 mg/kg), entacapone failed to reach the 50% inhibition level.

TABLE 3

Percent inhibition of COMT activity by compounds F–J in homogenates of rat brain and liver, determined at 6 and 9 h after their administration by gastric tube. Results are means ± S.E.M. of 4 experiments per group.

|   | Liver | | Brain | |
|---|---|---|---|---|
|   | 6 h | 9 h | 6 h | 9 h |
| F | 70.2 ± 3.3 | 37.7 ± 4.2 | 10.3 ± 5.1 | 0.4 ± 7.1 |
| G | 77.8 ± 4.5 | 51.2 ± 3.7 | 28.2 ± 5.1 | 27.1 ± 5.0 |
| H | 82.8 ± 2.2 | 45.8 ± 10.3 | 17.1 ± 4.0 | 6.8 ± 2.7 |
| I | 74.0 ± 4.6 | 46.3 ± 10.6 | 33.0 ± 2.0 | 24.6 ± 6.8 |
| J | 68.6 ± 4.2 | 57.1 ± 8.1 | 12.1 ± 3.2 | 25.8 ± 2.1 |

Behavioural Testing

Amphetamine is a potent psychostimulant that depending on the dose administered produces increased locomotor behaviour and various stereotypical activities. A single low dose of amphetamine administered to rats leads to a characteristic response pattern consisting of increased locomotor activity, rearing, mild sniffing and head bobbing. Gradually increasing the dose of amphetamine results in a decrease in locomotion and rearing, which are replaced by focused stereotypes (repetitive, seemingly aimless behaviours performed in a relatively invariant manner) confined to a small area of the cage floor (Feldman, R. S., Meyer, J. S., Quenzer, L. F., Principles of Neuropharmacology, 1997, Sinauer Associates, Inc. Publishers, Sunderland, Mass.). The cerebral dopaminergic system has traditionally been crucial to the ability of amphetamine to stimulate locomotor activity and stereotypical behaviours. With respect to the anatomic substrates of amphetamine action, there is evidence that stimulation of dopaminergic activity in the nucleus accumbens is responsible for amphetamine-induced locomotor activity, whereas stimulation of dopaminergic activity in the caudate-putamen is linked with focused stereotypes produced by high doses of amphetamine.

As predicted, low doses of amphetamine (0.5 and 2.0 mg/kg, s.c.) were found to produce dose-dependent increases in horizontal activity and rearing, with no evidence of stereotyped behavior (FIGS. 5 and 6). By contrast, a high dose of amphetamine (4.0 mg/kg, s.c.) was found to produce no further increase in locomotor activity, but resulted in the appearance of stereotypies which lasted for 250 s during the 600 s observation period. Tolcapone (30 mg/kg, p.o.) administered 6 h before amphetamine challenge was found to significantly increase locomotor activity in rats treated with 0.5 and 2.0 mg/kg amphetamine. By contrast, in rats given 4.0 mg/kg amphetamine, tolcapone produced a marked decrease in locomotor activity and increased two-fold the duration of stereotyped behavior. Rats treated with entacapone (30 mg/kg, p.o.) or compound B six hours before amphetamine challenge presented the same pattern of locomotor activity and stereotyped behaviour as their corresponding controls.

Conclusion

Compounds of formula I are very potent catechol-O-methyl transferase (COMT) inhibitors and have potentially valuable pharmaceutical properties in the treatment of some central and peripheral nervous system disorders where inhibition of O-methylation of catecholamines may be of therapeutical benefit, such as Parkinson's disease and parkinsonian disorders, gastrointestinal disturbances, edema formation states and hypertension. The possibility to use a long acting COMT inhibitor with limited access to the brain, such as compound B, opens new perspectives in said therapies by improving selectivity and prolong COMT inhibition. This is particularly important when thinking of treating patients afflicted by Parkinson's disease and taking L-DOPA plus a peripheral AADC inhibitor. Due to the possibility that COMT inhibitors which have easy access to the brain may cause excessive dopaminergic stimulation, namely by inducing dyskinesia and mental confusion in L-DOPA treated patients, the use of a substance such as compound B is expected to be devoid of such effects yet possessing the benefits of a long acting substance.

The invention disclosed herein is exemplified by the following examples of preparation, which should not be construed to limit the scope of the disclosure. Alternative pathways and analogous structures may be apparent to those skilled in the art.

EXAMPLE 1

1-(3,4-Dihydroxy-5-nitrophenyl)-2-phenyl-1-ethanone

A solution of 20 g (82.64 mmol) of O-benzylvanillin in 200 mL of dry tetrahydrofuran was slowly added to a stirred solution of benzyl magnesium chloride (103.30 mmol) in 150 mL of diethylether at 10° C. over 20 min, and the reaction mixture was then boiled for 10 min, cooled, quenched with a mixture of ice and dilute hydrochloric acid and evaporated at reduced pressure. The residue was dissolved in dichloromethane, the solution washed with brine, dried with sodium sulphate and the solvent was evaporated under reduced pressure leaving a crystalline residue that was recrystallised from diethylether and petroleum ether. 1-(4-Benzyloxy-3-methoxyphenyl)-2-phenyl-1-ethanol was obtained as white crystals, m.p. 97 to 98° C.

A solution of 10 g (30 mmol) of the above secondary alcohol in 90 mL of dichloromethane and 30 mL of diethylether was cooled to 0° C. and 7.5 g of Celite$^R$ was added at once with stirring, followed by 9 g (90 mmol) of chromium trioxide. The reaction mixture was stirred overnight at room temperature, filtered, and the filtrate was evaporated at reduced pressure. The crystalline residue was recrystallised from a mixture of dichloromethane and diethylether, yielding 1-(4-benzyloxy-3-methoxyphenyl)-2-phenyl-1-ethanone as white crystals, m.p 134 to 135° C.

A solution of 5.9 g, (17.8 mmol) of the above ketone in a mixture of dichloromethane (60 mL) and 30% hydrobromic acid in acetic acid (27 mL) was stirred for 1.5 h at room temperature and then the dichloromethane was evaporated at reduced pressure and the reaction mixture was poured onto 200 mL of an ice/water mixture. The precipitate formed was filtered off, and dried under vacuum to provide 1-(4-hydroxy-3-methoxyphenyl)-2-phenyl-1-ethanone as beige crystals, m.p. 107 to 108° C.

To a solution of 3.87 g (16 mmol) of the above intermediate in 40 mL of acetic acid there was added 1.4 mL (17.6 mmol) of 12.6 M nitric acid under cooling to 10° C. and the reaction mixture was stirred for 30 min at room temperature and then poured over an ice/water mixture. The precipitate formed was filtered off, washed with water and dried giving 1-(4-hydroxy-3-methoxy-5-nitrophenyl)-2-phenyl-1-ethanone as a yellow powder m.p. 129 to 130° C.

The above nitroderivative (3.76g, 13 mmol) was boiled with a mixture of azeotropic hydrobromic acid (37 mL) and 30% HBr in acetic acid (18 mL) for 16 hours and the cooled reaction mixture was poured onto a mixture of ice/water. The precipitate formed was filtered off, washed thoroughly with water and recrystallised from acetic acid to give the desired product as yellow crystals m.p. 181 to 182° C.

EXAMPLES 2–12

By the application of the above described technique and related procedures known to those skilled in the art, and using appropriate metalorganic reagents the following compounds were prepared:

1-(3,4-dihydroxy-5-nitrophenyl)-2-(4-hydroxyphenyl)-1-ethanone 1-(3,4-dihydroxy-5-nitrophenyl)-2-(2-methylphenyl)-1-ethanone 1-(3,4-dihydroxy-5-nitrophenyl)-2-(3-methylphenyl)-1-ethanone 1-(3,4-dihydroxy-5-nitrophenyl)-2-(4-methylphenyl)-1-ethanone 1-(3,4-dihydroxy-5-nitrophenyl)-2-(4-butylphenyl)-1-ethanone 1-(3,4-dihydroxy-5-nitrophenyl)-2-(3,4-dimethylphenyl)-1-ethanone 1-(3,4-dihydroxy-5-nitrophenyl)-2-(3,4-dimethoxyphenyl)-1-ethanone 1-(3,4-dihydroxy-5-nitrophenyl)-2-(4-butyloxyphenyl)-1-ethanone 1-(3,4-dihydroxy-5-nitrophenyl)-2-(1-methyl-5-indolyl)-1-ethanone 1-(3,4-dihydroxy-5-nitrophenyl)-2-(3,4-methylenedioxyphenyl)-1-ethanone 1-(3,4-dihydroxy-5-nitrophenyl)-2-(2,4,6-trimethylphenyl)-1-ethanone

EXAMPLE 13

1-(3,4-Dihydroxy-5-nitrophenyl)-2-(2-methylphenyl)-1-ethanone

To a mixture of guaiacol (1.24 g, 10 mmol), o-tolylacetic acid (1.50 9, 10 mmol), and $ZnCl_2$ (5 g, 36.7 mmol) there was added $POCl_3$ (15 mL, 161 mmol) and the resulting suspension was stirred and heated to 80° C. for 1.5 h. The reaction mixture was cooled and poured onto ice/water and the resulting suspension was stirred at room temperature for 1 h and then extracted with ethyl acetate. The organic layer was separated, washed with brine and dried with sodium sulphate. Volatiles were evaporated under reduced pressure and the residue was dissolved in diethylether. The solution was extracted twice with 50 mL of 2N aqueous solution of NaOH and the combined aqueous layers were combined and acidified with hydrochloric acid to pH=2. The emulsion formed was extracted by ethyl acetate, and the organic layer was washed with brine, dried, and the solvent was evaporated under diminished pressure. The residue was chromatographed on a column of silica gel with a mixture of petroleum ether and ethyl acetate to give 1-(4-hydroxy-3-methoxyphenyl)-2-(2-methylphenyl)-1-ethanone as off white crystals, m.p. 79 to 81° C.

To a solution of 4.01 g (16 mmol) of the above intermediate in 40 mL of acetic acid, there was added 1.4 mL (17.6 mmol) of 12.6 M nitric acid under cooling to 10° C. and the reaction mixture was stirred for 30 min at room temperature and then poured over an ice/water mixture. The precipitate formed was filtered off, washed with water and dried giving 1-(4-hydroxy-3-methoxy-5-nitrophenyl)-2-(2-methylphenyl)-1-ethanone as a yellow powder m.p. 150 to 151° C.

The above nitroderivative (3.91 g, 13 mmol) was boiled with a mixture of azeotropic hydrobromic acid (37 mL) and 30% HBr in acetic acid (18 mL) for 16 hours and the cooled reaction mixture was poured onto a mixture of ice/water. The precipitate formed was filtered off, washed thoroughly with water and recrystallized from acetic acid to give the desired product as yellow crystals m.p. 128 to 129° C.

EXAMPLES 14–21

By the application of the above described technique and related procedures known to those skilled in the art, and using appropriately substituted phenylacetic acids the following compounds were prepared:

1-(3,4-dihydroxy-5-nitrophenyl)-2-(4-carboxyphenyl)-1-ethanone 1-(3,4-dihydroxy-5-nitrophenyl)-2-(2-nitrophenyl)-1-ethanone 1-(3,4-dihydroxy-5-nitrophenyl)-2-(4-biphenyl)-1-ethanone 1-(3,4-dihydroxy-5-nitrophenyl)-2-(3-cyanophenyl)-1-ethanone 1-(3,4-dihydroxy-5-nitrophenyl)-2-(1-naphthyl)-1-ethanone 1-(3,4-dihydroxy-5-nitrophenyl)-2-(2-naphthyl)-1-ethanone 1-(3,4-dihydroxy-5-nitrophenyl)-2-(2-chlorophenyl)-1-ethanone 1-(3,4-dihydroxy-5-nitrophenyl)-2-(4-chlorophenyl)-1-ethanone

EXAMPLE 22

1-(3,4-Diacetoxy-5-nitrophenyl)-2-phenyl-1-ethanone

A suspension of 9.20 g (33.6 mmol) of 1-(3,4-dihydroxy-5-nitrophenyl)-2-phenyl-1-ethanone in 90 mL of dichloromethane was treated with 7.85 g (100 mmol) of acetylchloride, 7.51 g (95 mmol) of pyridine, and a catalytic amount of 4-dimethylaminopyridine. After 1 h of stirring at room temperature the solution formed was washed successively with ice-cold 0.2N hydrochloric acid, 1% aqueous solution of sodium bicarbonate and brine. The dried ($Na_2SO_4$) solution was evaporated under reduced pressure, and the residue recrystallised from a mixture of diethylether and petroleum ether giving the desired product as yellow crystals, m.p. 94 to 95° C.

EXAMPLES 23–27

By the application of the above described technique and related procedures known to those skilled in the art, and using appropriately substituted 1-(3,4-dihydroxy-5-nitrophenyl)-2-phenyl-1-ethanones and halogenides or anhydrides of acids, the following compounds were prepared:

1-(3,4-dimethoxymethyloxy-5-nitrophenyl)-2-phenyl-1-ethanone 1-(3,4-dibutyryloxy-5-nitrophenyl)-2-phenyl-1-ethanone
1-(3,4di(4tolyisulphonyloxy)-5-nitrophenyl)-2-phenyl-1-ethanone
1-(3,4-dibutyryloxycarbonyloxy-5-nitrophenyl)-2-phenyl-1-ethanone
1-(3,4-diacetoxy-5-nitrophenyl)-2-(4-acetoxyphenyl)-1-ethanone

What is claimed is:

1. A compound of formula I:

where $R_1$ and $R_2$ are the same or different and signify hydrogens, optionally substituted lower alkanoyl or aroyl groups, or optionally substituted lower alkylcarbamoyl groups; $R_3$, $R_4$ and $R_5$ are the same or different and signify hydrogens, optionally substituted saturated or partially unsaturated lower hydrocarbon residues, hydroxyls, optionally substituted lower alkoxy or aryloxy groups, optionally substituted aryl, optionally substituted alkanoyl or aroyl groups, lower alkanoylamino groups, lower dialkanoylamino groups, optionally substituted lower alkyloxycarbonyl or aryloxycarbonyl groups, optionally substituted carbamoyl, halogen, amino, lower alkylamino or lower dialkylamino groups, or taken together signify aliphatic or heteroaliphatic rings or aromatic or heteroaromatic rings, and pharmaceutically acceptable salts thereof.

2. A compound according to claim 1 comprising: 1-(3,4-dihydroxy-5-nitrophenyl)-2-phenyl-1-ethanone; 1-(3,4-dihydroxy-5-nitrophenyl)-2-(2-methylphenyl)-1-ethanone; 1-(3,4-dihydroxy-5-nitrophenyl)-2-(4-chlorophenyl)-1-ethanone; 1-(3,4-dihydroxy-5-nitrophenyl)-2-(1-naphthyl)-1-ethanone; 1-(3,4-dihydroxy-5-nitrophenyl)-2-(2-naphthyl)-1-ethanone or 1-(3,4-dihydroxy-5-nitrophenyl)-2-(4-biphenyl)-1-ethanone.

3. A method of treating a subject afflicted by some central and peripheral nervous system disorders, where a reduction in the O-methylation of catecholamines may be of therapeutical benefit, such as Parkinson's disease and parkinsonian disorders, gastrointestinal disturbances, edema formation states and hypertension, which comprises administering to the subject an amount of a compound according to claim 1 effective to treat said diseases in the subject.

4. A method of treating a subject afflicted by some central and peripheral nervous system disorders, where a reduction in the O-methylation of catecholamines may be of therapeutical benefit, such as Parkinson's disease and parkinsonian disorders, gastrointestinal disturbances, edema formation states and hypertension, which comprises administering to the subject an amount of a compound according to claim 2 effective to treat said diseases in the subject.

5. A pharmaceutical composition comprising a therapeutically effective amount of a compound according to claim 1 in combination with a pharmaceutically acceptable carrier.

6. A pharmaceutical composition comprising a therapeutically effective amount of a compound according to claim 2 in combination with a pharmaceutically acceptable carrier.

7. A method of manufacturing a medication for treating a subject afflicted by central or peripheral nervous system disorders comprising combining a compound according to claim 1 with a pharmaceutically acceptable carrier.

8. A method of manufacturing a medication for treating a subject afflicted by central or peripheral nervous system disorders comprising combining a compound according to claim 2 with a pharmaceutically acceptable carrier.

9. A method of manufacturing a medication for treating Parkinson's Disease and parkinsonian disorders, gastrointestinal disturbances, edema formation states and hypertension comprising combining a compound according to claim 1 with a pharmaceutically acceptable carrier.

10. A method of manufacturing a medication for treating Parkinson's Disease and parkinsonian disorders, gastrointestinal disturbances, edema formation states and hypertension comprising combining a compound according to claim 2 with a pharmaceutically acceptable carrier.

11. A pharmaceutical composition according to claim 5, further comprising L-DOPA and a peripheral aromatic L-amino acid decarboxylase (AADC) inhibitor.

12. A pharmaceutical composition according to claim 6, further comprising L-DOPA and a peripheral aromatic L-amino acid decarboxylase (AADC) inhibitor.

* * * * *